US 7,141,542 B2
(12) United States Patent
Cowan et al.

(10) Patent No.: US 7,141,542 B2
(45) Date of Patent: Nov. 28, 2006

(54) METHOD FOR STABILIZING BIOMOLECULES IN LIQUID FORMULATIONS

(75) Inventors: Siu Man L. Cowan, Lewis Center, OH (US); Vincent McGinniss, Sunbury, OH (US); Donna T. Palmer, Sunbury, OH (US); Steven M. Risser, Reynoldsburg, OH (US); Richard S. Brody, Worthington, OH (US)

(73) Assignee: Ventaira Pharmaceuticals, Inc., Columbus, OH (US)

( * ) Notice: Subject to any disclaimer, the term of this patent is extended or adjusted under 35 U.S.C. 154(b) by 0 days.

(21) Appl. No.: 10/020,799

(22) Filed: Nov. 30, 2001

(65) Prior Publication Data

US 2002/0110524 A1 Aug. 15, 2002

Related U.S. Application Data

(60) Provisional application No. 60/250,491, filed on Dec. 1, 2000.

(51) Int. Cl.
*A61K 38/00* (2006.01)
*A61K 38/28* (2006.01)
*A61K 31/715* (2006.01)

(52) U.S. Cl. .................... 514/2; 514/3; 514/53; 514/54
(58) Field of Classification Search ................ 424/45; 514/2, 3, 53, 54
See application file for complete search history.

(56) References Cited

U.S. PATENT DOCUMENTS

| 4,659,012 | A |   | 4/1987  | Coffee                 |
|-----------|---|---|---------|------------------------|
| 4,829,996 | A |   | 5/1989  | Noakes                 |
| 4,851,211 | A | * | 7/1989  | Adjei et al. ..... 424/40 |
| 5,385,685 | A | * | 1/1995  | Humphreys et al. ... 252/174.17 |
| 5,578,567 | A |   | 11/1996 | Cardinaux              |
| 5,653,987 | A | * | 8/1997  | Modi et al. ...... 424/400 |
| 5,660,166 | A |   | 8/1997  | Lloyd                  |
| 5,813,614 | A |   | 9/1998  | Coffee                 |
| 6,105,571 | A |   | 8/2000  | Coffee                 |
| 6,105,877 | A |   | 8/2000  | Coffee                 |
| 6,123,068 | A |   | 9/2000  | Lloyd                  |
| 6,158,431 | A |   | 12/2000 | Poole                  |
| 6,302,331 | B1|   | 10/2001 | Dvorsky                |
| 2003/0173219 | A1 |  | 9/2003 | Davies et al.          |

FOREIGN PATENT DOCUMENTS

| EP | 0-234-842    |   | 9/1987  |
|----|--------------|---|---------|
| HU | 62473        | * | 5/1993  |
| JP | 51116806     | * | 10/1976 |
| SU | 818619       | * | 4/1981  |
| WO | WO 94/14543  |   | 7/1994  |
| WO | WO 95/26235  |   | 10/1995 |
| WO | WO 98/29097  |   | 7/1998  |
| WO | WO 99/01463  |   | 1/1999  |
| WO | WO 99/07478  |   | 2/1999  |
| WO | WO 99/33853  |   | 7/1999  |
| WO | WO 99/42153  |   | 8/1999  |
| WO | WO 99/49981  |   | 10/1999 |
| WO | WO 00/35524  |   | 6/2000  |
| WO | WO 00/38770  |   | 7/2000  |
| WO | WO 00/66206  |   | 11/2000 |

* cited by examiner

*Primary Examiner*—Alton Pryor
(74) *Attorney, Agent, or Firm*—Frost Brown Todd LLC

(57) ABSTRACT

The invention is directed to a stable formulation of a biologically active protein useful for aerosol delivery to the respiratory tract of a patient in need of treatment comprising:
(a) a carrier liquid comprising from about 10% to from about 100% V/V water and from about 0% to from about 90% V/V of an organic liquid;
(b) a biologically effective amount of a protein suspended or dissolved in a carrier liquid; and
(c) a stabilizing effective amount of a derivatized carbohydrate stabilizing agent suspended or dissolved in said carrier liquid.

The stable formulations of the invention may optionally contain about 0.1% to about 5.0% W/V of a pharmaceutically acceptable excipient.

21 Claims, No Drawings

METHOD FOR STABILIZING BIOMOLECULES IN LIQUID FORMULATIONS

CROSS-REFERENCE TO RELATED APPLICATIONS

The present application claims the benefit of U.S. Provisional Application No. 60/250,491, filed Dec. 1, 2000.

BACKGROUND OF INVENTION

This invention relates generally to the stabilization of biomolecules in solvent systems compatible with electrostatic or electrohydrodynamic aerosol devices, and specifically to the stabilization of biologically active proteins such as insulin in liquid systems.

Pulmonary delivery of therapeutic agents by means of inhaled aerosols is an area of increasing importance in the biotechnology and pharmaceutical industries. Electrostatic or electrohydrodynamic devices which are capable of generating inhalable aerosols with certain preferred properties frequently require liquid formulations containing one or more solvents such as water, an organic solvent such as an alcohol, or a mixture of water and at least one organic solvent.

Biological molecules, ("biomolecules") are frequently difficult to formulate in certain solvents or solvent systems (e.g., mixtures of water and organic solvents) because organic solvents tend to compromise the stability of the biomolecule in solution. Biomolecules dissolved or suspended in liquid solvent systems typically suffer from chemical or physical degradation, thereby resulting in a formulation with little or no shelf life. Stabilization of the biomolecule in a given solvent system is therefore necessary to sustain the activity a given biomolecule. In formulations for use with electrostatic or electrohydrodynamic aerosol devices, non-ionic stabilizers are preferable to ionic compounds.

Regarding proteins used in pharmaceutical applications, processing and storage conditions, which do not diminish a given protein's biological function, must be achieved. To prevent the loss of native conformation, proteins must be protected from the chemical decomposition (e.g. by deamidation) and physical instability, which results from the disruption of noncovalent interactions. Aggregation (fibrillation), precipitation, and adsorption (especially on hydrophobic surfaces) are examples of such disruption.

One of the most important and commonly used therapeutic proteins is insulin. Insulin tends to polymerize and form microscopic aggregates, which prevent the delivery of insulin in certain drug delivery systems. This aggregated insulin may not have required pharmacological properties and may induce abnormal immune response (Chawla et al., *Diabetes* 34: 420–425, 1985). Thus, maintenance of insulin's biological activity is essential for more traditional insulin administration such as portable/implantable continuous infusion pumps and controlled release polymeric devices and systems. Furthermore, insulin aggregation leads to significant reductions in biological potency and obstruction of delivery routes, thereby creating serious complications for drug delivery systems and diminishing the patient's abilities to control their blood glucose levels."Sluzky et al., *Biotechnology and Bioengineering* 40: 895–903 (1992). Thus, there is a need for a method for stabilizing insulin and other biomolecules in liquid formulations utilized in drug delivery systems.

Stabilization methodologies for certain biological molecules are known in the art. For example, WO 98/29097 discloses compositions for increasing bioavailabilty through muscosal delivery, which includes mixtures of bioactive agents, and hydrophobically derivatized carbohydrates in powdered form. Similarly, WO 99/33853 discloses derivatized carbohydrates, which can be used to form a variety of materials, including solid delivery systems.

U.S. Pat. No. 4,439,421 issued to Hooper et al. (1984) discloses a stabilized gamma globulin concentrate in dry form, which utilizes polysaccharides including, branched and unbranched polymers of five and/or six carbon sugars. U.S. Pat. No. 5,547,873 issued to Magneson et al. (1996) discloses a composition for stabilizing proteins for long-term dry storage, which includes a glass-forming sugar.

While being effective at stabilizing certain biomolecules under certain conditions, the related art deals primarily with dry power or other solid systems, and do not offer methods or compositions for stabilizing biomolecules in liquid solvent systems suitable for use in liquid-based aerosol systems, including electrostatic and electrohydrodynamic devices and systems.

SUMMARY OF INVENTION

The invention is directed to a stable liquid formulation of a biologically active protein useful for aerosol delivery to the respiratory tract of a patient in need of treatment comprising:

(a) a carrier liquid comprising from about 10% to from about 100% V/V water and from about 0% to from about 90% V/V of an organic liquid;

(b) a biologically effective amount of a protein suspended or dissolved in said carrier liquid; and (c) a stabilizing effective amount of a derivatized carbohydrate stabilizing agent suspended or dissolved in said carrier liquid.

The stable liquid formulations of the invention may optionally contain from about 0.1% to about 5.0% W/V of a pharmaceutically acceptable excipient.

The preferred embodiment of this invention comprises a method for stabilizing biomolecules in a solvent system which includes the steps of (a) making a solution or a suspension of the biomolecule in the solvent system; (b) adding a stabilizing composition to the solution or suspension, wherein the stabilizing composition comprises a sugar moiety having at least one alkyl chain attached to the sugar moiety; and, optionally (c) adding an excipient to said solution or suspension for enhancing the stabilizing effect of said stabilizing composition.

DETAILED DESCRIPTION OF INVENTION

The present invention relates to a stable formulation of a biologically active protein useful for aerosol delivery to the respiratory tract of a patient in need of treatment comprising:

(a) a carrier liquid comprising from about 10% to from about 100% V/V water and from about 0% to from about 90% V/V of an organic liquid;

(b) a biologically effective amount of a protein suspended or dissolved in a carrier liquid; and (c) a stabilizing effective amount of a derivatized carbohydrate stabilizing agent suspended or dissolved in said carrier liquid.

The stable liquid formulations of the invention may optionally contain from about 0.1% to about 5.0% W/V of a pharmaceutically acceptable excipient.

The present invention provides methods and compositions for formulating proteins in a carrier liquid, which may be water, organic solvents, or mixtures of water and organic solvents. As used herein the term "protein" includes polypeptides and peptides as well as proteins.

The liquid formulations of the invention contain stabilized biologically active proteins as the active agent. These novel formulations are stable over extended periods, and as such, provide distinct advantages over other methods of formulating proteins in liquids that are compatible with aerosol drug delivery devices.

The stabilizing agents useful in the formulations of the invention are derivatized carbohydrates such as those described in WO 98/29097, WO 99/01463, and WO 99/33853 the disclosures of which are herein incorporated by reference. The chemical structures of exemplary derivatized carbohydrate useful as stabilizing agents in the formulations of the invention are shown below.

C8-Trehalose

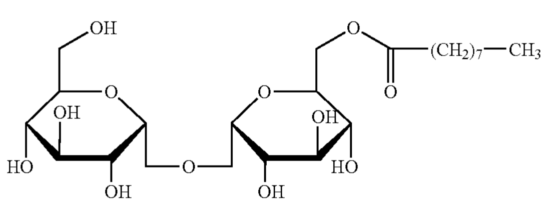

C12-Glucopyranoside

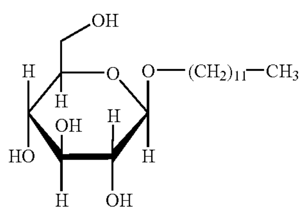

C8-Glucopyranoside

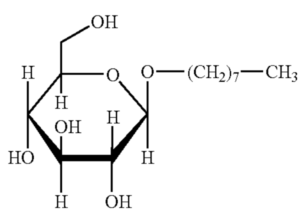

C16-Trehalose

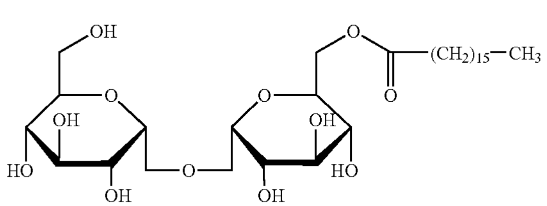

The choice of a particular derivatized carbohydrate-stabilizing agent will depend on the physical and chemical properties of the protein being stabilized, the concentration of the protein, and the composition of the carrier liquid. As used herein, the phrase, "stabilizing effective amount" means the amount of derivatized carbohydrate that must be used to produce a pharmaceutical product having a commercially reasonable shelf life at controlled room temperature or under refrigeration. In general, a "commercial reasonable" shelf life will be at least 9-months with 12-months being preferred. As would be recognized by one skilled in this art, a shelf life of greater than 12-months is desired but less than 9-months of shelf life may be acceptable under some circumstances.

In general, the derivatized carbohydrate stabilizing agents useful in the liquid formulations of the invention should be selected so that the stabilizing agent is soluble in the carrier liquid. However, the derivatized carbohydrate may be suspended in the carrier liquid and still provide good stabilization. The choice of a particular stabilizing agent will be made taking into consideration the physical and chemical characteristics of the protein to be stabilized and the particular carrier liquid chosen for the stabilized liquid formulation.

The derivatized carbohydrate stabilizing compounds useful herein include a sugar molecule modified by the addition of at least one aliphatic hydrocarbon chain (alkyl or alkenyl moiety) to the sugar molecule. The sugars compatible with the present invention include monosaccharides and polysaccharides. Various embodiments of this invention utilize trehalose, sucrose, glucose, maltose, and galactose as the sugar moiety. Each sugar used as a stabilizing composition has at least one alkyl or alkenyl chain attached to said sugar moiety at carbon 1, 2, 3, 4, 5, or 6. The aliphatic hydrocarbon chain is either saturated or unsaturated and includes about 6 to 18 carbon atoms which may be straight chain or branched chain.

The following Example 1 describes the preparation of octyl-(C8) trehalose, which is a preferred stabilizing agent for use in the compositions of the invention. The method described in Example 1 is modified from the method of Bottle and Jenkins, J. Chem. Soc. Chem. Commun. 385, 1984. The C8 and C12 glucopyranosides, n-dodecyl-β-D-glucopyranoside (Sigma D 8035) and n-octyl-β-D-glucopyranoside (Sigma 09882) were purchased from Sigma-Aldrich Corp., St. Louis, Mo., USA.

EXAMPLE 1

Preparation of Octyl-(C8) Trehalose

Anhydrous trehalose was prepared by dissolving trehalose dihydrate in pyridine (1 g in 3 ml) followed by removal of the solvent by distillation at atmospheric pressure. Anhydrous N,N-dimethylformamide (DMF) was prepared by distillation of DMF from $P_2O_5$ at 20 mmHg. The dry DMF was stored with molecular sieves (3 A) under Argon. To a reaction flask was added 16 g anhydrous trehalose in 240 ml dry DMF under argon gas with a drying tube. The solution was heated to 42° C. and stirred or sonicated for 10 minutes to promote dissolving of the sugar. The flask was cooled to 0° C. using an ice bath and thereafter was added 7.36 g triphenylphosphine (M.W. 262.3), and 3.28 g caprylic acid (M.W. 144.2) under argon. The mixture was stirred with a magnetic stirrer on the ice bath until a solution was obtained.

Thereafter, was added to the solution 5.6 ml (5.76 g) di-isopropyl azodicarboxylate (DIAD, M.W. 202.2, d 1.027) dropwise in a 15-minute period. The mixture was kept at 0° C. and stirred while adding DIAD under argon. Stirring was continued at room temperature for 72 hours under anhydrous argon. The resulting product was purified using column chromatography and characterized by NMR.

Following the procedure of Example 1, other derivatized carbohydrate stabilizing agents may be prepared by utilization of the appropriate starting fatty acid. The structure of selected derivatized carbohydrate stabilizing agents is shown below.

The term "stable" or "stability" is used to mean preservation of the biological activity of a protein in the liquid formulations of the invention.

The term "suspension" as used herein is given its ordinary meaning and refers to particles of protein or aggregates of particles of protein suspended in the carrier liquid. Where the biologically active protein is dissolved in the carrier liquid a solution rather than a suspension is formed.

The stable formulations of the invention are useful for preparing aerosols for the delivery of therapeutic proteins to the respiratory tract. The term "respiratory tract" includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli, which then lead to the ultimate respiratory zone, the alveoli, or deep lung. Gonda, I. "Aerosols for delivery of therapeutic and diagnostic agents to the respiratory tract," in Critical Reviews in Therapeutic Drug Carrier Systems, 6:273–313, (1990). Usually, the deep lung, or alveoli, is the primary target of inhaled therapeutic aerosols for systemic delivery. As used herein, the term "respiratory tract" is additionally meant to include administration of the stable formulations via the nares.

The term "biologically active protein" includes proteins and polypeptides that are used for diagnostic and reagent purposes as well as proteins and polypeptides that are administered to patients as the active drug substance for treatment of a disease or condition. Contemplated for use in the compositions of the invention are proteins and polypeptides such as enzymes, e.g., ascorbate oxidase, peroxidase, catalase, glucose oxidase, chymotripsin, lactate dehydrogenase and glucose-6-phosphate dehydrogenase; antibodies, e.g. Herceptin® (trastuzumab), Orthocione OKT®3 (muromonab-CD3); hormones, e.g., insulin and human growth hormone (HGH); growth factors, e.g., fibroblast growth factor (FGF), nerve growth factor (NGF), human growth hormone releasing factor (HGHRF), and cytokines, e.g., leukemia inhibitory factor (LIF), granulocyte-colony stimulating factor (G-CSF), granulocyte macrophage-colony stimulating factor (GM-CSF), interleukin-6 (IL-6), interleukin-11 (IL-11), interleukin-9 (IL-9), oncostatin-M (OSM), and Factor VIII.

In addition to enzymes and antibodies used in diagnostic tests or in in vitro assays, the term "biologically active" includes proteins that are administered to a patient in a "pharmaceutically effective amount" to treat a disease or condition. As would be recognized by one skilled in the art, by "pharmaceutically effective amount" is meant an amount of a pharmaceutical protein having a therapeutically relevant effect on the disease or condition to be treated. A therapeutically relevant effect relieves to some extent one or more symptoms of the disease or condition in a patient or returns to normal either partially or completely one or more physiological or biochemical parameters associated with or causative of the disease or condition. Specific details of the dosage of a particular active protein drug may be found in its labeling, i.e., the package insert (see 21 CFR § 201.56 & 201.57) approved by the United States Food and Drug Administration.

As would be recognized by the skilled artisan, the stable protein formulations of the invention may optionally include "minor amounts", that is from about 0.05% to about 5.0% W/V and preferably from about 0.05% to from about 1.0% of a pharmaceutically acceptable excipient. Pharmaceutically acceptable excipients are those recognized by the FDA as being safe for use in humans. Additives such as, surfactants, e.g., ethoxylated dodecyl alcohol, antioxidants, e.g., Vitamin E and ascorbic acid, antimicrobials, e.g., parabens and suspending agents, e.g., povidone are contemplated for use herein.

While the selection of any particular excipient is within the skill of the art, as will be appreciated, the decision regarding whether to add an excipient and if so which one, will be made taking into account the purpose of the excipient in a specific formulation of a biologically active protein.

In order to be pharmaceutically acceptable any formulation excipient used in a stable formulation of the invention should be recognized by the FDA as safe for use in humans. Additionally, an excipient should have no effect or minimal effect on the stability of the protein in the formulations of the invention or on the sprayability of the formulations using and electrostatic spraying means.

In general, where the biologically active protein is suspended, rather than dissolved in the carrier liquid, the particle size of the protein particles will range from about $0.01\mu$ to about $10.0\mu$ in diameter. If delivery of the protein to the deep lung is the object, the particle size of the protein should preferably range from about $0.01\mu$ to about $5.0\mu$ in diameter and more preferably from about $0.01\mu$ to about $3.0\mu$ in diameter. If delivery of the protein to the upper respiratory tract is the object, the particle size of the protein may range from about $5.0\mu$ to about $10.0\mu$ in diameter.

If the biologically active protein is dissolved in the carrier liquid, the droplet size of the aerosol produced by the electrostatic spraying means should be from about $1.0\mu$ to about $10.0\mu$ in diameter and more preferably from about $1.0\mu$ to about $3.0\mu$ in diameter. For example, for delivery of a biologically active protein to the deep lung, aerosol droplets of from about $1.0\mu$ to about $5.0\mu$ in diameter are preferred.

The method of the invention utilizes a dispensing device for comminuting the liquid suspensions claimed herein. Dispensing devices are known which produce a finely divided spray of liquid droplets by electrostatic means (sometimes referred to as 'electrohydrodynamic' means). Electrohydrodynamic ("EHD") sprayers are particularly useful in medicine for the administration of medicaments by inhalation. Various EHD devices are known in the art, as for example, those described in U.S. Pat. Nos. 6,105,877 and 6,068,199.

The droplet spray in such EHD devices is generated by applying an electric field to a liquid located at a spray head or spray edge. The potential of the electric field is sufficiently high to provide comminution of electrically charged liquid droplets from the spray head. The electrical charge on the droplets prevents them from coagulating via mutual repulsion.

Prior to inhalation of the aerosol by the patient, it is usually necessary to partially or wholly remove the electric charge from the aerosol droplet spray produced by the electrohydrodynamic comminution device in a controlled manner.

Although other methods may be used, the principal method used to effect comminution discharge utilizes a discharging electrode having a sharp or pointed edge and located downstream from the spray head of the EHD device. The discharging electrode produces a cloud of charged ions from the surrounding air having an opposite electrical charge of equal magnitude to that on the comminuted liquid spray (aerosol). In use, the ion cloud is attracted towards, collides with, and thereby neutralizes the liquid aerosol spray.

Although the protein/ethanol suspensions of the invention are particularly suited for use with EHD devices as would be recognized by one skilled in the art such suspensions are aerosolizable using other aerosol generating devices such as a nebulizer; see WO 99/44664 which describes a pulmonary dosing system and a method for supplying to a patient a predetermined amount of respirable therapeutically active material.

A preferred embodiment of the present invention includes a method for stabilizing biomolecules in a solvent system which includes the steps of (a) making a solution or a suspension of the biomolecule in the solvent system; and (b) adding a stabilizing composition to the solution or suspension, wherein the stabilizing composition comprises a sugar moiety having at least one alkyl chain attached to the sugar moiety. This preferred method includes the optional step of adding an adjuvant to said solution or suspension for enhancing the stabilizing effect of said stabilizing composition. This adjuvant is selected from the group consisting of metal ions, phenol, methylparaben, buffer salt, surfactants, and polymers. Preferred metal ions include calcium ions or zinc ions.

According to the preferred embodiment, solvent systems compatible with this invention include water, organic solvents, and mixtures of water and organic solvents. Preferred organic solvents include ethanol, isopropyl alcohol, butanol, isobutanol, perfluorocarbons, glycerol, polyethylene glycol, and propylene glycol.

The solvent systems contemplated by this invention also include various interfaces considered hostile to protein stability. These interfaces include air-water interfaces, oil-water interfaces, solid-water interfaces, aqueous-organic interfaces, or combinations of such interfaces. The methods and compositions of the present invention promote the stability of proteins or other biological molecules encountering such hostile environments.

When making a solution or a suspension of the biomolecule in the solvent systems of the present invention, the pH of the solution or suspension must be adjusted based on the solubility characteristics of the biomolecule being dissolved or suspended. Thus, an acceptable pH range is determined by the biomolecule in question as well as by the choice of solvent system. the preparation of insulin for use in the various liquid formulations of the invention.

Tables 1–4 present HPLC data reflecting percent insulin activity retained over a period of days by utilizing the stabilizing compositions of the present invention. Note that the shaking motion promotes aggregation of insulin in solution through interaction with hydrophobic surfaces. These data demonstrate the effectiveness of modified trehalose and modified glucose in promoting protein stability in various solvent systems.

EXAMPLE 2

Lyophilized human insulin, supplied from Roche Biochemical Co., was used. To obtain the desired pH, 100 mg of insulin was first dissolved in the appropriate buffer, e.g., 2.667 ml of 10 mM PBS buffer, pH 7.4 (Supplied from Sigma, P 3813); 356 ul of this dissolved insulin was aliquoted into 15 ml polypropylene conical tubes, which were later used for the 20 mg/ml suspension samples. To make the insulin suspension samples at a concentration of 1.5 mg/ml, 26.67 ul of the dissolved insulin was aliquoted into 15 ml polypropylene conical tubes. The conical tubes were then sealed with punctured parafilm, and frozen overnight at ~–15° C. to –20° C. The following day the frozen insulin samples were lyophilized to a fine, free-flowing powder using a bench top Labconco Freeze Dry System with Stoppering Tray. This process was started two or three days prior to the start of the experiment. Each liquid insulin formulation was prepared in duplicate. The lyophilized insulin powder was suspended in 667 μl of carrier liquid . The Day "0" samples were immediately diluted with 9.33 ml of 0.1% TFA so the final concentration of the insulin samples would fit within the HPLC standard curve. The diluted samples were then analyzed by reversed phase HPLC method using standard techniques known to the art. Samples were maintained at 37° C. with and without shaking, at 40° C. with shaking and at room temperature with no shaking. A Labline environmental incubator/shaker was used at 37° C. and at 40° C. while shaking at 220 rpm. Once the next time-point was reached, the samples were again diluted with 9.33 ml of 0.1% TFA and analyzed for insulin activity. In the preparation of all samples containing insulin, care was taken not to sonicate or vigorously shake any preparation of insulin due to the possibility of precipitation. Inversion was used to gently mix. Percent activity retained was determined by high-performance liquid chromatography (HPLC).

The data presented in Tables 1–4 illustrates various aspects of the stabilized protein formulations of the invention. The biologically active protein used in the various formulations was human insulin. Example 2 describes

TABLE 1

Insulin in Ethanol/Water Carrier Liquid.

| Protein | Carrier Liquid ETOH | $H_2O$ | Stabilizer | Time Period At 37° C. | Excipient | Activity Retained (%) | Shaking (rpm) | pH |
|---|---|---|---|---|---|---|---|---|
| Insulin | 80% | 20% | None | 2.5 months | None | 11% | NA | 5.4 |
| Insulin | 80% | 20% | None | 2.5 months | None | 42% | NA | 7.4 |
| Insulin | 80% | 20% | None | 2.5 months | $ZnCl_2$ | 81% | NA | 7.4 |
| Insulin | 80% | 20% | None | 7 days | None | 18% | 220 | 7.4 |
| Insulin | 80% | 20% | None | 7 days | $ZnCl_2$ | 24% | 220 | 7.4 |
| Insulin | 80% | 20% | None | 7 days | Trehalose | 41% | 220 | 7.4 |
| Insulin | 80% | 20% | C8-glucose | 7 days | None | 20% | 220 | 7.4 |
| Insulin | 80% | 20% | C8-trehalose | 7 days | None | 21% | 220 | 7.4 |
| Insulin | 80% | 20% | C16-trehalose | 7 days | None | 48% | 220 | 7.4 |
| Insulin | 80% | 20% | C12-glucose | 7 days | None | 72% | 220 | 7.4 |

TABLE 1-continued

Insulin in Ethanol/Water Carrier Liquid.

| Protein | Carrier Liquid ETOH | H₂O | Stabilizer | Time Period At 37° C. | Excipient | Activity Retained (%) | Shaking (rpm) | pH |
|---|---|---|---|---|---|---|---|---|
| Insulin | 80% | 20% | None | 7 Days | Glucose | 0 | 220 | 7.4 |

TABLE 2

Insulin in Ethanol/PEG Carrier Liquid.

| Protein | Solvent or Solvent System | Stabilizer | Time Period At 37° C. | Excipient | Activity Retained (%) | Shaking (rpm) |
|---|---|---|---|---|---|---|
| Insulin | 80% ETOH/ 20% PEG | None | 14 days | None | 0% | NA |
| Insulin | 80% ETOH/ 20% PEG | C8-glucose | 14 days | None | 88% | NA |
| Insulin | 80% ETOH/ 20% PEG | C12-Glucose | 7 days | None | 1% | 220 |
| Insulin | 80% ETOH/ 20% PEG | None | 7 days | glucose | 4% | 220 |

TABLE 3

Carrier Liquid - Water Only.

| Protein | Solvent or Solvent System | Stabilizer | Time Period At 37° C. | Adjuvant | Activity Retained (%) | Shaking (rpm) | pH |
|---|---|---|---|---|---|---|---|
| Insulin | 100% H₂O | None | 10 days | None | 0% | 220 | 7.6 |
| Insulin | 100% H₂O | None | 10 days | ZnCl₂ | 0% | 220 | 7.6 |
| Insulin | 100% H₂O | C8-glucose | 10 days | None | 100% | 220 | 7.6 |
| Insulin | 100% H₂O | None | 14 days | None | 1% | 220 | 7.4 |
| Insulin | 100% H₂O | C8-trehalose | 14 days | None | 94% | 220 | 7.4 |
| Insulin | 100% H₂O | C16-trehalose | 14 days | None | 52% | 220 | 7.4 |

TABLE 4

Insulin in Water/ETOH (70:30) Carrier Liquid at 40° C.

| CARRIER LIQUID H₂O/ ETOH | STABILIZING AGENT | TIME IN DAYS | EXCIPIENT | ACTIVITY RETAINED (%) | SHAKING (RPM | PH |
|---|---|---|---|---|---|---|
| 70:30 | None | 7 | None | 13 | 220 | 7.4 |
| 70:30 | C8-Glucose | 7 | None | 91 | 220 | 7.4 |
| 70:30 | C12-Glucose | 7 | None | 1 | 220 | 7.4 |

The data in Table 1 illustrates that the choice of a particular derivatized carbohydrate stabilizer will depend on the particular protein being stabilized and further as illustrated by the data in Tables 2, 3 and 4 on the particular carrier liquid utilized in the stabilized formulations of the invention. In an ethanol/water (80:20) carrier liquid, the preferred stabilizer for insulin is C12-glucose, while in a totally aqueous carrier liquid (100% water), the preferred stabilizer for insulin is C8-glucose or C8-trehalose.

While various preferred embodiments have been shown and described, it will be understood that there is no intention to limit the invention by such disclosure, but rather, is intended to cover all modifications and alternate constructions falling within the spirit and scope of the invention as defined in the appended claims.

What is claimed:

1. A stable liquid formulation of a therapeutically active protein consisting essentially of:
   (a) a carrier liquid consisting essentially of from about 10% v/v to about 100% v/v water and from about 0% to from about 90% v/v of an organic liquid;
   (b) a biologically effective amount of said protein suspended or dissolved in said carrier liquid;
   (c) a stabilizing effective amount of a stabilizing component consisting of a derivatized carbohydrate suspended or dissolved in said carrier liquid; and optionally a pharmaceutically acceptable excipient
wherein said derivatized carbohydrate is a sugar moiety selected from the group consisting of trehalose, sucrose, glucose, maltose, and galactose modified by the addition of at least one alkyl or alkenyl hydrocarbon group attached to said sugar moiety at carbon 1, 2, 3, 4, 5 or 6 and wherein said hydrocarbon group contains about 6 to about 18 carbon atoms which may be straight chain or branched chain, and wherein said therapeutically active protein is not an enzyme.

2. A stable formulation according to claim 1 wherein said pharmaceutically acceptable excipient is present in an amount from about 0.1% w/v to about 5.0% w/v.

3. A stable formulation according to claim 1 wherein said therapeutically active protein is selected from the group consisting of antibodies, antigens, hormones and cytokines.

4. A stable formulation according to claim 3 wherein said therapeutically active protein is a hormone.

5. A stable formulation according to claim 4 wherein said therapeutically active protein is insulin.

6. A stable formulation according to claim 3 wherein said therapeutically active protein is a cytokine.

7. A stable liquid formulation of a therapeutically active protein consisting essentially of:
  (a) a carrier liquid consisting essentially of from about 10% v/v to about 100% v/v water and from about 0% to from about 90% v/v of an organic liquid;
  (b) a biologically effective amount of said protein suspended or dissolved in said carrier liquid; and
  (c) a stabilizing effective amount of a derivatized carbohydrate stabilizing agent suspended or dissolved in said carrier liquid;
wherein said derivatized carbohydrate is a sugar moiety selected from the group consisting of trehalose, sucrose, glucose, maltose, and galactose modified by the addition of at least one alkyl or alkenyl hydrocarbon group attached to said sugar moiety at carbon 1, 2, 3, 4, 5 or 6 and wherein said hydrocarbon group contains from about 6 to about 18 carbon atoms which may be straight chain or branched chain, and wherein said therapeutically active protein is Factor VIII.

8. A stable formulation according to claim 1 wherein said carrier liquid consists essentially of from about 20% v/v to from about 100% v/v water.

9. A stable formulation according to claim 8 wherein said carrier liquid consists essentially of about 50% v/v water and about 50% v/v organic solvent.

10. A stable liquid formulation of a therapeutically active protein consisting essentially of:
  (a) a carrier liquid consisting essentially of from about 10% v/v to about 100% v/v water and from about 0% to about 90% v/v of an organic liquid selected from the group consisting of ethanol, isopropyl alcohol, butanol, isobutanol, perfluorocarbons, glycerol, polyethylene glycol, propylene glycol, and mixtures thereof;
  (b) a biologically effective amount of said protein suspended or dissolved in said carrier liquid; and
  (c) a stabilizing effective amount of a derivatized carbohydrate stabilizing agent suspended or dissolved in said carrier liquid;
wherein said derivatized carbohydrate is a sugar moiety selected from the group consisting of trehalose, sucrose, glucose, maltose, and galactose modified by the addition of at least one alkyl or alkenyl hydrocarbon group attached to said sugar moiety at carbon 1, 2, 3, 4, 5 or 6 and wherein said hydrocarbon group contains about 6 to about 18 carbon atoms which may be straight chain or branched chain, and wherein said therapeutically active protein is not an enzyme.

11. A stable formulation according to claim 10 wherein said organic liquid is selected from the group consisting of ethanol, glycerol, polyethylene glycol, propylene glycol, and mixtures thereof.

12. A stable liquid formulation of a therapeutically active protein consisting essentially of:
  a) a carrier liquid consisting essentially of from about 10% v/v to about 100% v/v water and from about 0% to about 90% v/v of an organic liquid;
  (b) a biologically effective amount of said protein suspended or dissolved in said carrier liquid; and
  (c) a stabilizing effective amount of a derivatized hydrocarbon stabilizing agent suspended or dissolved in said carrier liquid;
wherein said stabilizing agent is selected from the group consisting of C8-trehalose, C8-glycopyranoside, and mixtures thereof, and wherein said therapeutically active protein is not an enzyme.

13. A stable liquid formulation of a therapeutically active protein consisting essentially of:
  (a) a carrier liquid consisting essentially of from about 10% v/v to about 100% v/v water and from about 0% to about 90% v/v of an organic liquid;
  (b) a biologically effective amount of said protein suspended in said carrier liquid; and
  (c) a stabilizing effective amount of a derivatized carbohydrate stabilizing agent suspended or dissolved in said liquid carrier;
wherein said derivatized carbohydrate is a sugar moiety selected from the group consisting of trehalose, sucrose, glucose, maltose, and galactose modified by the addition of at least one alkyl or alkenyl hydrocarbon group attached to said sugar moiety at carbon 1, 2, 3, 4, 5 or 6 and wherein said hydrocarbon group contains from about 6 to about 18 carbon atoms which may be straight chain or branched chain, and wherein said therapeutically active protein is not an enzyme.

14. A stable formulation according to claim 13 wherein the particle size of said protein in suspension is from about 0.01 μ to about 10.0 μ.

15. A stable formulation according to claim 14 wherein the particle size of said protein in suspension is from about 5.0 μ to about 10.0 μ.

16. A stable formulation according to claim 15 wherein the particle size of said protein in suspension is from about 0.1 μ to about 3.0 μ.

17. A stable formulation according to claim 2 wherein said formulation contains from about 0.1% to about 5.0% of a pharmaceutically acceptable excipient.

18. A stable formulation according to claim 1 wherein said protein is dissolved in the carrier liquid.

19. A stable formulation according to claim 18 wherein said pharmaceutically acceptable excipient is present in an amount from about 0.1% w/v to about 5.0w/v.

20. A method of formulating a stable liquid formulation of a therapeutically active protein useful for aerosol delivery to the lower respiratory tract of a patient in need of treatment consisting essentially of the mixing of components comprising:
  (a) a carrier liquid which consists essentially of from about 10% v/v to from about 100% v/v water and from about 0% v/v to from about 90% v/v ethanol;

(b) a biologically effective amount of said protein suspended or dissolved in said carrier liquid; and (c) a stabilizing effective amount of a derivatized carbohydrate stabilizing agent;

wherein said derivatized carbohydrate comprises a sugar moiety selected from the group consisting of trehalose, sucrose, glucose, maltose, and galactose modified by the addition of at least one alkyl or alkenyl hydrocarbon group attached to said sugar moiety at carbon 1, 2, 3, 4, 5, or 6 and wherein said hydrocarbon group contains about 6 to 18 carbon atoms which may be straight chain or branched chain, and wherein said therapeutically active protein is not an enzyme.

21. An apparatus for delivery of a therapeutically active protein to the lower respiratory tract of a patient comprising an electrostatic or an electrohydrodynamic device capable of generating inhalable aerosols, said device containing a stable liquid formulation of a therapeutically active protein consisting essentially of:

(a) a carrier liquid consisting essentially of from about 10% v/v to about 100% v/v water and from about 0% to about 90% v/v of an organic liquid;

(b) a biologically effective amount of said protein suspended or dissolved in said carrier liquid; and (c) a stabilizing effective amount of a derivatized carbohydrate stabilizing agent suspended or dissolved in said carrier liquid;

wherein said derivatized carbohydrate is a sugar moiety selected from the group consisting of trehalose, sucrose, glucose, maltose, and galactose modified by the addition of at least one alkyl or alkenyl hydrocarbon group attached to said sugar moiety at carbon 1, 2, 3, 4, 5 or 6 and wherein said hydrocarbon group contains about 6 to about 18 carbon atoms which may be straight chain or branched chain, and wherein said therapeutically active protein is not an enzyme.

* * * * *